(12) United States Patent
Baroni et al.

(10) Patent No.: US 7,484,403 B2
(45) Date of Patent: Feb. 3, 2009

(54) METHOD AND DEVICE FOR DETERMINING AT LEAST ONE DYNAMIC PROPERTY OF A DEFORMABLE SOLID OR FLUID MATERIAL

(75) Inventors: Patrick Baroni, Les Ulis (FR); Hakima Mendil, Thiais (FR); Laurence Noirez, Orsay (FR)

(73) Assignee: Commissariat A l'Energie Atomique (FR)

( * ) Notice: Subject to any disclaimer, the term of this patent is extended or adjusted under 35 U.S.C. 154(b) by 233 days.

(21) Appl. No.: 11/497,640

(22) Filed: Aug. 2, 2006

(65) Prior Publication Data

US 2007/0180938 A1 Aug. 9, 2007

(30) Foreign Application Priority Data

Oct. 27, 2005 (FR) .................... 05 10988

(51) Int. Cl.
*G01N 11/10* (2006.01)
(52) U.S. Cl. .................................... 73/54.37
(58) Field of Classification Search ............. 73/54.39, 73/841, 866, 54.22, 54.01
See application file for complete search history.

(56) References Cited

U.S. PATENT DOCUMENTS

| | | | | |
|---|---|---|---|---|
| 4,072,045 A | * | 2/1978 | Kopito | 73/54.37 |
| 4,299,118 A | * | 11/1981 | Gau et al. | 73/54.35 |
| 4,404,855 A | * | 9/1983 | Leidenfrost | 73/747 |
| 4,554,821 A | * | 11/1985 | Kiesewetter et al. | 73/54.07 |
| 4,566,324 A | * | 1/1986 | Vinogradov et al. | 73/54.39 |
| 4,694,685 A | * | 9/1987 | Dick | 73/104 |
| 5,080,484 A | | 1/1992 | Schneider et al. | |
| 5,270,781 A | * | 12/1993 | Singh et al. | 356/32 |
| 5,314,731 A | * | 5/1994 | Yoneda et al. | 428/429 |
| 5,789,045 A | * | 8/1998 | Wapner et al. | 428/34.4 |
| 5,861,946 A | | 1/1999 | Hudson et al. | |
| 6,581,438 B1 | * | 6/2003 | Hall et al. | 73/53.01 |
| 7,024,921 B2 | * | 4/2006 | Sutton | 73/54.04 |
| 7,188,515 B2 | * | 3/2007 | Burns et al. | 73/54.05 |

FOREIGN PATENT DOCUMENTS

| | | |
|---|---|---|
| CN | 1 456 386 A | 11/2003 |
| CN | 1 587 145 A | 3/2005 |
| DE | 102 01 234 A1 | 7/2003 |
| FR | 2 574 180 A | 6/1986 |
| FR | 2 624 272 A | 6/1989 |

\* cited by examiner

*Primary Examiner*—Hezron Williams
*Assistant Examiner*—John Fitzgerald
(74) *Attorney, Agent, or Firm*—Alston & Bird LLP

(57) ABSTRACT

Method of determining at least one dynamic characteristic of a sample of a deformable solid or fluid material, comprising: the contacting of said sample (24, 42) with at least one interaction surface (23, 25, 41a, 41b); the application of a relative movement between said sample (24, 42) and said interaction surface (23, 25, 41a, 41b); and the measurement (26) of at least one dynamic or kinematic quantity in respect of the sample (24, 42) and/or said interaction surface (23, 25, 41a, 41b), wherein said interaction surface (23, 25, 41a, 41b) has an intrinsic wettability with respect to the material that is higher than that of metals.

Device for implementing this method.

According to particular embodiments, said interaction surface (23, 25) is made of high-density sintered ceramic or made of single crystal silicon or germanium, preferably having a zero open porosity and an arithmetic mean roughness parameter of less than 12.5 μm and preferably between 0.4 and 1.6 μm.

29 Claims, 4 Drawing Sheets

METHOD AND DEVICE FOR DETERMINING AT LEAST ONE DYNAMIC PROPERTY OF A DEFORMABLE SOLID OR FLUID MATERIAL

The invention relates to a method of determining at least one dynamic characteristic of a sample of a deformable solid or fluid material and to a device for implementing such a method. The invention applies in particular to rheology and viscosity measurements.

Within the context of the invention, the term "deformable solid" corresponds to a material having an elastic response to strain levels of greater than 0.01%.

Rheology is a discipline that deals with dynamic properties of liquids and materials by examining their response to the action of a stress [G. Couarraze and J. L. Grossiord, "Initiation à la Rhéologie [*Introduction to Rheology*]", published by Lavoisier]. This discipline rapidly became established as the technique for characterizing fluids, but also materials exhibiting behavior intermediate between a perfect solid and a model (Newtonian) fluid, that is to say the very great majority of materials that can be conventionally called "viscoelastic fluids" and contain an increasing number of substances owing to the appearance of a great variety of novel products exhibiting complex behavior, for example emulsions, foams, muds, gels, biogels, pastes, cementitious slurries, petroleum products and, of course, polymers and elastomers.

Rheological measurements are generally carried out using commercial devices, in particular rheometers having an axial symmetry of movement (rotation) in which the material can be stressed either in an oscillatory mode with frequencies generally ranging between 0.01 rad/s to 100 rad/s (viscoelastic property and viscosity measurements), or in continuous mode, that is to say by imposing a continuous rotation (study of flow properties, generally called nonlinear rheology), or a constant stress (study of stress relaxation and creep). Very many imposed-stress or imposed-strain rheometers exist on the market. These rheometers are used daily in industry, and research and development, as instruments for characterizing fluids, particularly plastics. They are constructed and sold by specialized companies (TA-Instruments, Rheometric, Bohlin, Physica, Haake, Anton Paar, Thermo Rheo, etc.) having acquired experience with this type of instrumentation over a long period.

It is also known to use piezorheometers, which use the micron-scale oscillating displacement of a piezo-electric membrane to impose a strain field on a sample. It is acknowledged by the rheological community that measurements performed with a piezo-rheometer are similar to those of conventional rheometers [J. Crassous et al., Journal of Rheology, 49, 851, (2005)].

Whether performed using a conventional rheometer or a piezorheometer, the rheological measurements are entirely dependent on the interaction conditions between the sample and an interaction surface of the rheometer (sample support). When the interaction of the material with the support is not strong enough, the resistance of product to the imposed strain (or stress) field measured by the rheometer is not fully taken into account (partial or total slip conditions). It is therefore essential to establish conditions in which there is no slip of the material relative to the substrate, without which no quantitative information about the solid contribution (elastic modulus) and the viscous contribution (viscous modulus or loss modulus) is possible.

Until recently, it was considered that non-slip conditions were guaranteed for most rheology experiments, in particular with regard to low-viscosity fluids. Recent studies have shown that this is not always the case.

P. Martinoty's group has succeeded in minimizing the slip factors in studies carried out on thin samples (thickness less than 150 µm) using a piezorheometer equipped with appropriately treated interaction surfaces. These interaction surfaces are conventional glass surfaces of optical quality, grooved in the direction perpendicular to the movement (these grooves produce macroscopic defects several microns in size, while the mean operating thickness is around 20-30 microns) or subjected to chemical treatments or to irradiation in order to cause surface charges to appear. Under these (non-slip) conditions, it has been shown that the rheological response of a standard polymer (polystyrene) film is not that of a visco-elastic fluid but that of a gel. This is manifested by the invariance of the elastic modulus with frequency [D. Collin and P. Martinoty, Physica A. 320, 235, (2003)].

The use of the method developed by this team places substantial constraints on the operator. This is because slip is only avoided under conditions in which the substrate undergoes very small displacements relative to the product, which requires the use of very thin samples [G. Ash et al., "Les capteurs en instrumentation [*Sensors in instrumentation*]", Dunod, 5th edition, 506, (2001)] and means that special attention must be paid to the surface finish of the supports. To give an example, the strain levels applied by D. Collin and P. Martinoty are of the order of 0.01% and the measurements are made with small thicknesses (<150 µm)—the displacement is of the order of 0.01 µm. Conventional rheometers do not allow measurements to be made with such low displacements, and consequently it is necessary to use piezo-rheometers, which are expensive and require considerable fine tuning. Furthermore, piezorheometers are particularly difficult to employ for studies as a function of temperature, since the piezoelectric constants are in general highly dependent on temperature (pyroelectric effect) and increase the uncertainty in the measurement the higher the temperature. In addition, above the Curie temperature (generally 200° C.), the piezoelectric properties are lost.

Another drawback of the technique used by D. Collin and P. Martinoty is that the surface treatments for minimizing slip can be altered mechanically, chemically or over time, thereby posing measurement reproducibility problems.

The object of the invention is to provide a method and a device for performing rheological and/or viscosity measurements, making it possible to minimize or eliminate the effects of slip between a sample and its support, while still being simpler to implement, less expensive and more reproducible, and/or making it possible to overcome the limitations of piezorheometers in studies as a function of temperature.

According to the invention, such an object is achieved by a method of determining at least one dynamic characteristic of a sample of a deformable solid or fluid material, comprising the steps of:

contacting said sample with at least one interaction surface;

applying a relative movement between said sample and said interaction surface; and measuring at least one dynamic or kinematic quantity in respect of the sample and/or said interaction surface, and determining, from said measurement, at least one dynamic characteristic of said sample, wherein in that said interaction surface has an intrinsic wettability with respect to the sample that is higher than that of metals.

The expression "dynamic or kinematic quantity" is understood, for example, to mean a frequency, a stress, an amplitude, a strain, a velocity, an acceleration or a force. The term "dynamic characteristic" is understood to mean a characteristic specific to the sample, such as an elastic modulus and/or a viscous modulus, determined from the measurement of one or more dynamic or kinematic quantities.

The use of an interaction surface according to the invention allows the interaction between the sample and the support to be improved to such a point that the slip is greatly reduced or essentially eliminated even under the operating conditions of conventional rheometers (larger displacements and thicker samples than in the case of measurements using a piezorheometer), thus relaxing the constraints that the prior art imposed on the experimenter. Furthermore, an interaction surface according to the invention is of greater stability, thereby reducing the costs and improving the reproducibility of the measurements.

According to particular modes of implementing the method of the invention:

- said interaction surface may have an arithmetic mean roughness parameter of less than 12.5 μm, preferably between 0.1 and 3.2 μm and advantageously between 0.4 and 1.6 μm;
- said interaction surface may have a zero open porosity;
- said interaction surface may have a surface energy at room temperature of greater than 1.2 J/m$^2$;
- said interaction surface may consist of a "high-density" sintered ceramic, typically composed essentially of oxides, nitrides and/or carbides and having a density of greater than 2.7; in particular, said ceramic may consist of or be prepared from $Al_2O_3$, MgO, $SiO_2$, SiC, $ZrO_2$ or a mixture of these compounds, and/or may be obtained by sintering at a pressure of 1 MPa or higher and at a temperature of 1500° C. or higher;
- said interaction surface may consist of a single crystal, in particular a single crystal based on silicon, germanium, oxides or carbides, such as $Al_2O_3$, MgO or SiC;
- the method may comprise the steps of contacting said sample with at least two interaction surfaces and applying a relative movement between said two interaction surfaces;
- said dynamic or kinematic quantity may be a relative quantity of the sample with respect to the interaction surface, for example a relative displacement;
- said dynamic or kinematic quantity may be chosen from a frequency, a stress, an amplitude, a strain, a velocity, an acceleration and a force.

The above object is also achieved by means of a device according to the invention, comprising:

- at least one interaction surface intended to be brought into contact with said sample; and
- a means for imposing a relative movement between said sample and said interaction surface, wherein said interaction surface has an intrinsic wettability with respect to the material that is higher than that of metals.

According to particular embodiments of the device of the invention:

- said interaction surface may be as defined above;
- the device may comprise at least one sensor for measuring at least one dynamic or kinematic quantity in respect of the sample and/or said interaction surface;
- said sensor and said means for imposing a relative movement between said sample and said interaction surface may be placed on the same axis;
- said means for imposing a relative movement between said sample and said interaction surface may include a second interaction surface and also includes an optional means for imposing a relative movement between said two interaction surfaces; and
- said sensor may be chosen from a force sensor, a torque sensor and a displacement sensor.

Other features, details and advantages of the invention will become apparent on reading the description in conjunction with the appended drawings given by way of example and representing, respectively:

FIG. 1b, a representation of the contact angle between the drop and the surface of FIG. 1a;

In a conventional rheometer, for example of the ARES type from TA-Instruments, a sample of the material to be studied is placed in contact with and between two supports (interaction surfaces), generally metal plates, the purpose of which is to transmit a deformation stress to the sample. The strain of the sample may result from the application of a force or from the application of a strain (imposed-strain rheometer). The movement may be generated by the lower plate, the upper plate remaining fixed, or vice versa. In a "true" imposed-strain rheometer, the motor that causes the sample to deform is connected to the first sample support plate and the force sensor is connected to the second plate. The sensor applies a force so as to stabilize the shaft of the second plate. This measurement method faithfully takes account of the strain of the sample, since the measurement and the strain are decoupled. The support here consists of two separate plates.

Figure 2:
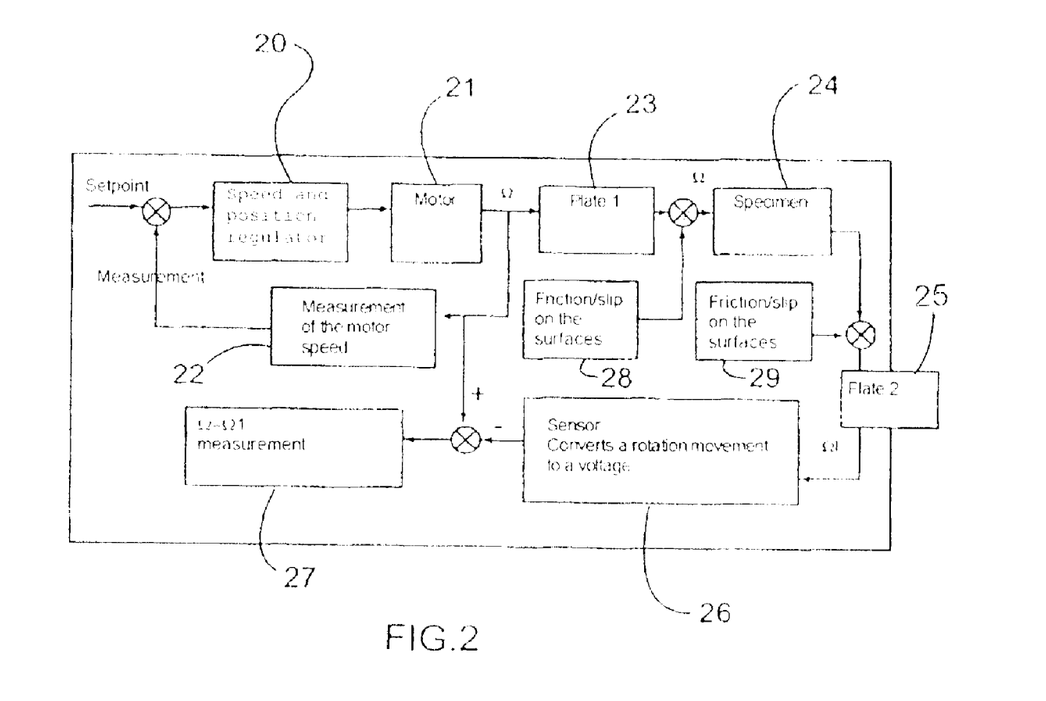
FIG. 2, a schematic representation of the simplified feedback loop of an imposed-strain rheometer.

The diagram in FIG. 2 shows the simplified feedback loop of an imposed-strain rheometer. The diagram makes it possible in particular to locate where the contribution of the sample/support (plates) interface occurs in the measurement loop. The regulator 20 for controlling the motor 21 that causes the deformation receives a setpoint and transmits it to the motor. The motor 21 generates an angular movement or an angular velocity $\Omega$. The displacement is then controlled by means of a controller 22 so as to maintain a displacement equivalent to what is required. The motor 21 is in contact with the first plate 23, which interacts with the sample 24. The transmission of the displacement to the sample is entirely determined by its properties of adhesion between the two materials.

The movement actually transmitted to the sample is $\Omega'$. Finally, the transmission of the strain to the second plate 25 (called the measurement plate) equipped with a sensor 26, is also determined by the quality of the adhesion between the sample 24 and said measurement plate 25. Let $\Omega 1$ be the movement read by this sensor. The final measurement of the feedback loop results in the measurement of $\Omega - \Omega 1$, where $\Omega$ corresponds to the torque that determines the angular velocity imposed by the motor and Ω1 corresponds to the torque needed to stop the sensor shaft or the phase shift measured thereat (block 27).

Possible losses of adhesion, and therefore of torque Ω transmission between the plates and the sample are represented in the diagram by the "friction or slip" blocks identified by the references 28 and 29. They are therefore not taken into account in the measurement. These losses are wrongly considered to be nonexistent or negligible in most rheological measurements (determined under linear conditions). The inventors have shown that taking these transmission losses into account fundamentally modifies the dynamic response spectrum of the sample, and consequently the knowledge of the physical properties of the material.

According to the invention, the problems associated with slip in rheological measurements can be solved satisfactorily using supports, or interaction surfaces, having specific properties defined in particular using parameters such as the wettability, the open porosity and the roughness (arithmetic mean roughness parameter).

Figure 1A:
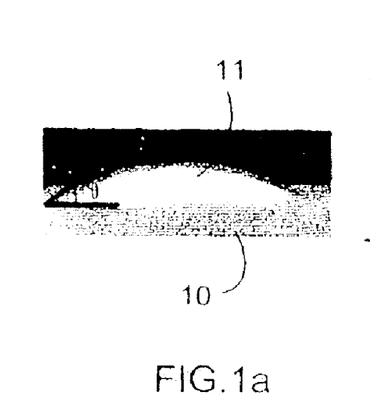
FIG. 1a, a photograph of a drop on a surface.
Figure 1B:
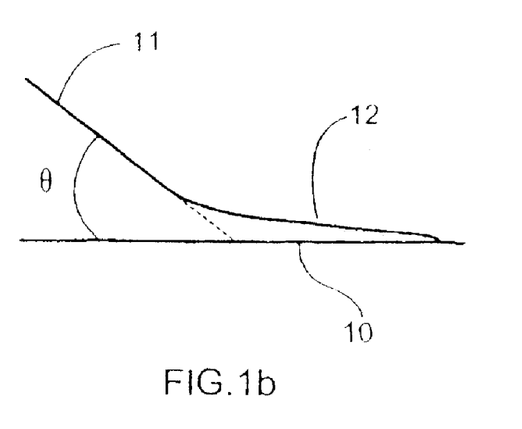

The wettability of a surface, which depends on the surface energy, may be determined by measuring the spread of a drop of a fluid substance or deformable solid spreading over a surface, illustrated by FIGS. 1a and 1b. The contact angle θ (FIG. 1b) provides a simple and effective measurement of the interaction between the sample and the substrate [T. Young, Phil. Trans. Roy. Soc. London, 95, 65, (1805)]. Young's equation connects the contact angle θ with the surface energy of the substance through the relationship: $\sigma_{SG} = \sigma_{SL} + \sigma_{LG} \cdot \cos\theta$, where $\sigma_{SG}$ is the surface tension or energy of the solid-gas region, $\sigma_{SL}$ is the surface energy or tension of the boundary region between the support and the sample, and $\sigma_{LG}$ is the surface energy or tension of the liquid-gas surface.

In particular, the inventors recommend performing a dynamic wettability measurement, consisting in observing the variation as a function of time of said contact angle θ between the surface 10 and the drop 11. The relationship between the contact angle and the surface energy is given by Young's equation [Phil. Trans. Roy. Soc. A 95, 65 (1805)]. Other measurement methods known in the field may however be employed. The interaction surfaces according to the invention preferably have a lower contact angle θ than metals or metal alloys that are not chemically treated (oxidation, nitriding or the like) and also glasses (fused silicates) for the same substance. According to the invention, it is preferable for the interaction surface to be chosen in such a way that the contact angle θ between it and the material to be studied (deformable solid or fluid) varies over the course of time in order to achieve, asymptotically, a zero angle (complete wettability) or an angle substantially smaller (typically less than 45° in the case of water) than those obtained with surfaces commonly used to make the sample supports in commercial rheometers, that is to say metals, particularly stainless steels and aluminum, or fused silicate glasses (in the case of these materials, the contact angle of water exceeds 60°).

Figure 3:
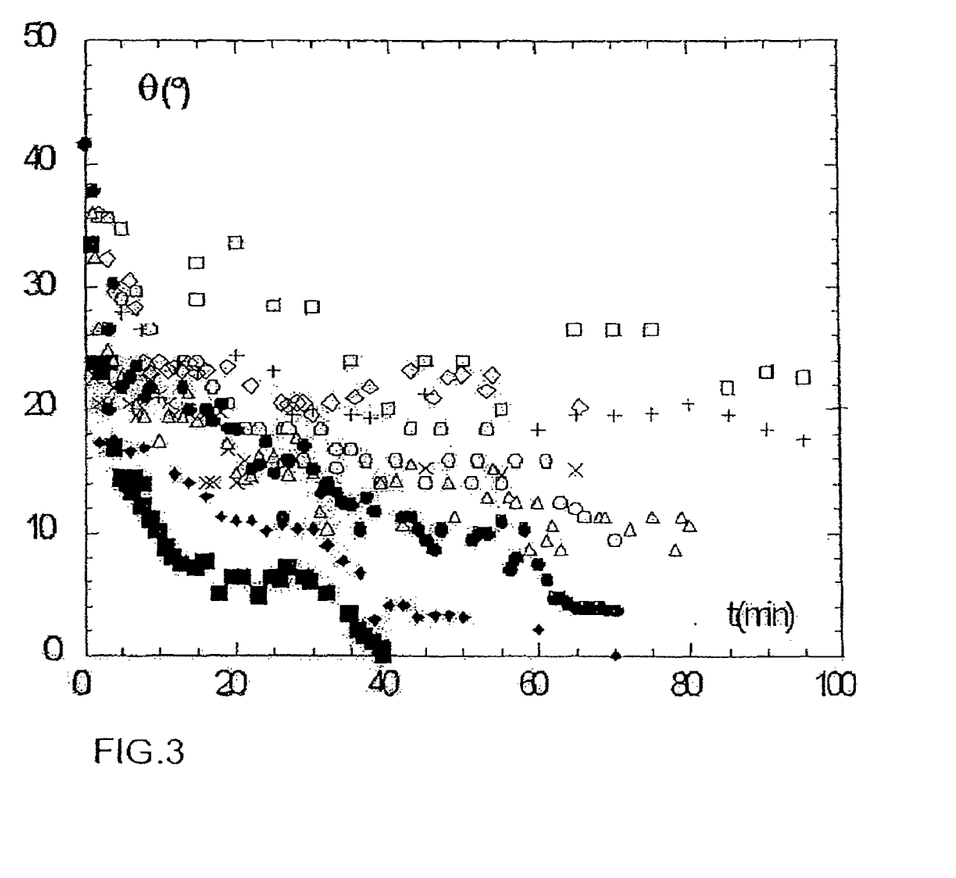
FIG. 3, the variation of the contact angle θ as a function of time t (in s) for a drop of polybutyl acrylate deposited on various surfaces.

FIG. 3 shows the variation in the contact angle θ as a function of time t (in s) for a drop of polybutyl acrylate deposited on various surfaces: X2CrNi18-9 stainless steel (highly alloyed steel with 0.02% carbon, 18% chromium and 9% nickel) [NF EN 10 269 standard] (□); glass (◇); aluminum (+); high-density sintered alumina (polycrystalline $Al_2O_3$) (●); high-density $ZrO_2$ (X); CTU092 (the acronym stands for Céramique Technique Usinable [*Machinable Engineering Ceramic*]—final nomenclature) (Δ); single crystal SiC (■); alpha-phase single crystal $Al_2O_3$ (♦); and single crystal silicon (○). For the measurements to be comparable, these materials have almost identical surface finishes, that is to say roughness parameters of around $R_a$=0.8 to 1.6 μm (see below for the definition of the parameter $R_a$).

The contact angle θ was measured using a camera provided with a macroscopic objective, taking images at 0.25 to 1 image/min. The images were digitized and recorded on a digital medium, and then the angle between the drop front and the substrate was determined by digital image processing.

Owing to the differences in surface energy, various wetting tests were carried out. A first test was performed with distilled water on aluminum, stainless steel, silicon and nonporous alumina. This preliminary measurement showed that, in a few moments, the drop of water was spread more on alumina and silicon than on aluminum, stainless steel or glass (silicate). Alumina, and also its crystalline form (corundum), and silicon gave excellent wettability with respect to polybutyl acrylate, quantitatively after a time of 20 minutes, θ<20° for the ceramic and silicon, whereas θ>30° on aluminum or stainless steel.

The wetting tests were carried out under standard rheological operating conditions. In the example that follows, the sample was a standard polymer, polybutyl acrylate, which is a hydrophobic organic compound of low molecular weight ($M_w$=5000 g/mol; polydispersity=1.1) measured at room temperature (25° C.). The variation in the contact angle of polybutyl acrylate as a function of time is illustrated in FIG. 3 and the reference time for the comparison was chosen to be 70 minutes.

The tests showed that the poorest wetting was that obtained with a stainless steel support (□ symbol) (304L(X2CrNi18-9) stainless steel) [NF EN 10 269 standard] since the angle obtained 70 minutes after depositing the drop was θ=24°±1°. In increasing order of wettability was then glass (◇ symbol) with an angle θ=20±1° followed by aluminum (+ symbol) (AG3 containing 97% aluminum and 3% magnesium), with a contact angle θ=19.5°. It may be noted in FIG. 5 that the molecular part (defined by the thin film extending upstream of the drop—reference 12 in FIG. 1b) is completely absent on aluminum, and also on stainless steel and on glass. This means that the surface energy was not high enough to generate the molecular part allowing complete spreading of the sample. Moreover, in the case of glass, aluminum and stainless steel, it was noted that the contact angle reached a non-zero steady-state value very rapidly (t=20 min) equivalent to that measured 100 min later. The wetting with the polymer was therefore never complete in the case of aluminum, stainless steel and glass (silicate) surfaces.

In the case of ceramics, and in particular high-density $ZrO_2$ (FIG. 3: X symbol), it may be noted that the molecular part is visible at the drop, even though the contact angle stabilizes at θ=15°±1°.

Figure 5A:
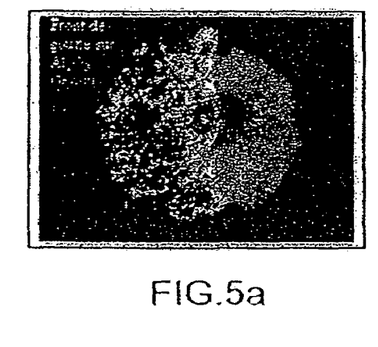
FIGS. 5a and 5b, a photograph of a drop front on an alumina ($Al_2O_3$) surface and an aluminum surface, respectively.
Figure 5B:
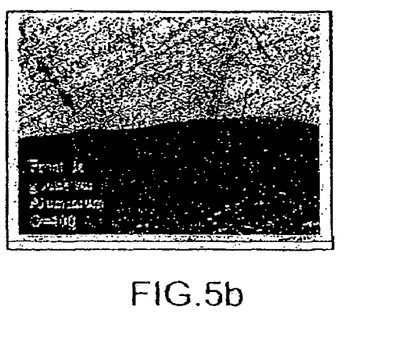

In the case of deposition on high-density sintered alumina (polycrystalline $Al_2O_3$) (FIG. 3: ● symbol) and CTU902 (FIG. 3: Δ symbol), the molecular part is very well developed (see FIG. 5a). The measurement showed that the contact angle θ decreased very quickly and that, after 70 min, it was less than 10°. Two hours after deposition of the drop, the wetting of the part was complete, the angle θ then being zero. Comparison with a silicon surface shows that the curve of the contact angle as a function of time for sintered alumina can be superimposed on that with CTU902. These conditions are optimal, the surface tension of the test liquid being lower than the critical surface tension of the sample support.

Finally, the single crystal SiC (■) provided complete wettability in a time of 40 minutes and single crystal alumina (♦) in about 1 hour.

Although almost all the rheology experiments were carried out with aluminum or stainless steel sample supports, the inventors have discovered that it is advantageous to use supports having a high wettability. The above study shows that the best wettability result is obtained using ceramics of the single crystal or high-density sintered polycrystalline, CTU902 or $Al_2O_3$ type, single crystal SiC (FIG. 3: ■ symbol) and single crystal silicon (FIG. 3: ○ symbol).

According to the invention, it is generally preferable for at least one interaction surface (sample support) to consist of high-density sintered ceramic or of single crystals. A ceramic is defined as a material composed of at least one element having an electronegativity of greater than 1.7 according to the Pauling-Miller criterion ["The Nature of the Chemical Bond", 3rd edition (1960) published by Cornell University Press, Ithaca, N.Y., United States]. For the purpose of the present invention, a "high-density sintered ceramic" corresponds more precisely to an agglomerate of oxides, nitrides or carbonates obtained after binder removal, under high pressure (>1 MPa) and high temperature (>1500° C.), the density of which is typically higher than 2.7. This material is of recent design, having mechanical properties (hardness) similar to diamond and a zero open porosity index [ISO 5017].

It is advantageous to use ceramics derived from magnesium, aluminum and silicon, which result in a combination of electronegativity and nonsaturation of the external atomic layers. It should be noted that most metal oxides may constitute ceramics, with the exception of iron oxides or copper oxides, which do not form ceramics. The preferred ceramics according to the invention consist of, or are prepared from, $Al_2O_3$, MgO, $SiO_2$, SiC and $ZrO_2$. The preferred single crystals are single crystals based on Si or Ge (that is to say consisting of these elements in the pure state or those combined with O, C, or any other metalloid) and solid oxides and carbides such as $Al_2O_3$, MgO and SiC.

Moreover, it is preferable for said ceramic to furthermore possess acid-base properties so as to be able to develop ionic, acid-base, electrostatic or van der Waals interactions with the sample. Thus, a ceramic of MgO type may act as a base and attract more strongly compounds "acid" in nature, a ceramic of $Al_2O_3$ type is amphoteric and attracts acids and bases, while finally silicon is considered more to be an acid, attracting bases or the basic parts of materials. In addition, compounds of variable electronegativity, such as magnesium (1.3 on the Pauling-Miller scale), aluminum (1.5) or silicon (1.8), that is to say corresponding to a family of elements that can create covalent bonds, like germanium too, have the possibility of producing van der Waals, ionic or covalent bonds.

According to another embodiment, said at least one interaction surface may consist of an agglomerate or a single crystal of a material having a surface energy exceeding that of metals (>1.2 $J/m^2$ at room temperature) such as pure silicon. For comparison, the materials conventionally used for sample supports in rheology are the following: aluminum (with a surface energy of 0.7 $J/m^2$), stainless steels (0.7 to 1.1 $J/m^2$) and fused silicate glasses (between 0.2 and 0.3 $J/m^2$) (the surface energies being measured at room temperature).

According to a preferred embodiment, the interaction surface is a pore-free sintered material, more precisely the base constituent of the support is a very fine, hot-compression-molded powder [J. C. Chervin, "Céramiques et matériaux pour l'optique", dans "matériaux et joints d'étanchéité pour les hautes pressions" ["*Ceramics and materials for optics*", in "*high-pressure seals and materials*"], published by Lavoisier, Tec et Doc, 55 (1986); E. Mistler, "Tape Casting" Engineering Material Handbook, 4, Ceramic and Glass, ASM International, Materials Park, Ohio (1987); and A. C. Pierre, "Les Céramiques Techniques [*Ceramic Techniques*]", published by Septima, (1994).

The composition of said at least one interaction surface can vary and may consist of a combination, preferably in the form of an agglomerate, of the abovementioned materials.

Moreover, and insofar as several interaction surfaces are employed, these may differ in nature provided that they obey the aforementioned criteria and make it possible to ensure that there is no slip under the standard operating conditions of conventional rheometers.

The abovementioned ceramic or single crystal materials exhibit good intrinsic wettability. This means that their wettability is not dependent on a particular surface treatment, whether physical (by irradiation) or chemical, and is not liable to be impaired over the course of time.

Open porosity is defined according to the ISO 5017 standard. For example, a ceramic of CTU902 type, despite its particularly good wettability properties, is unsuitable for implementing the present invention as it is porous. The sample would pass through a porous surface, which is generally undesirable.

The roughness of the interaction surface is defined by means of the arithmetic mean roughness parameter $R_a$, which has the dimension of a length [ISO 1302 and 12085 standard]. This is the arithmetic mean of the height of the asperities on the surface of the support in contact with the sample. Advantageously, the parameter $R_a$ of an interaction surface according to the invention must be less than 12.5 μm and preferably have a variable mean undulation depth. Typically, the arithmetic mean roughness parameter will be between 0.1 and 3.2 μm, advantageously between 0.4 and 1.6 μm.

Figure 7A:
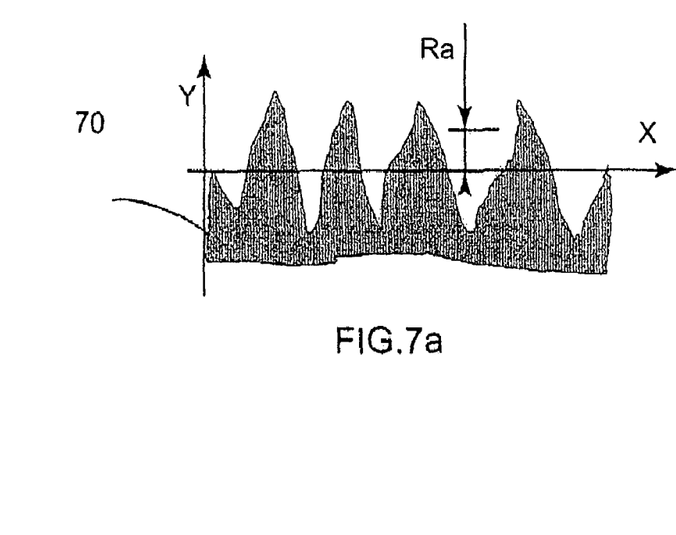
FIGS. 7a and 7b, a schematic representation of a cross section through the thickness of an interaction surface according to the invention after end-milling with diamond-tipped tools and a photograph of this same surface, respectively.
Figure 7B:
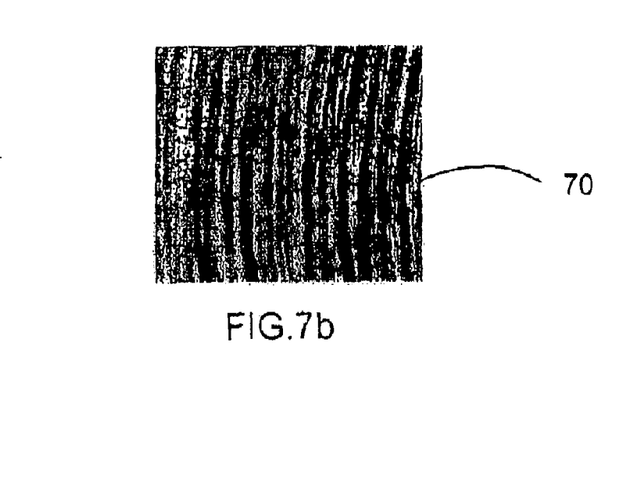

It is preferable for the interaction surface to be obtained from a plane surface of the constituent material of the support by carrying out an end-machining operation using a milling cutter or by using an abrasive powder having a grit size of the order of 1 micron: the arithmetic mean roughness parameter obtained is then around 0.5 μm. Alternatively, such interaction surfaces may also be obtained directly by means of a diamond milling cutter, making it possible to achieve the desired arithmetic mean roughness parameter, the diamond grit size corresponding to the level of roughness. FIGS. 7*a* and 7*b* show, in a cross-sectional view and a plane view respectively, an interaction surface obtained by using a diamond milling cutter. It may be seen that the roughness takes the form of a number of parallel grooves. However, unlike the known processes of the prior art, the orientation of the grooves relative to the direction of the relative movement between the sample and the interaction surface is not essential.

Preferably, the interaction surface is chemically and mechanically stable, having a compressive strength>400 MPa, a flexural strength>60 MPa and a Young's elastic modulus>100 GPa.

Figure 4A:
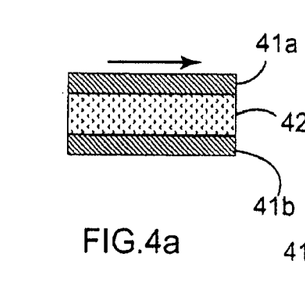
FIGS. 4a to 4g, schematic representations of various devices and methods according to the invention.
Figure 4B:
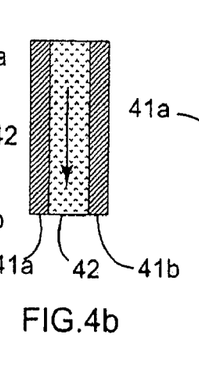
Figure 4C:
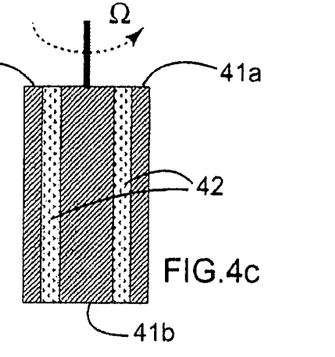
Figure 4D:
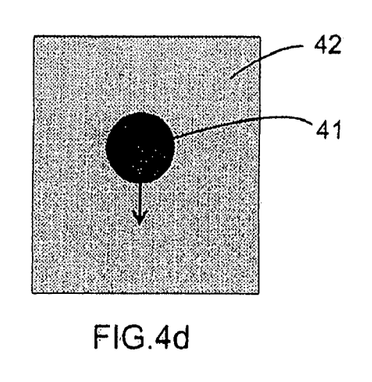
Figure 4E:
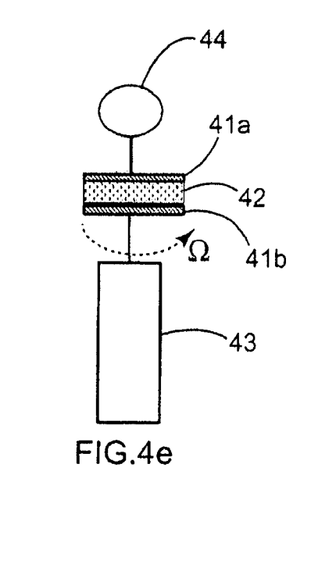
Figure 4F:
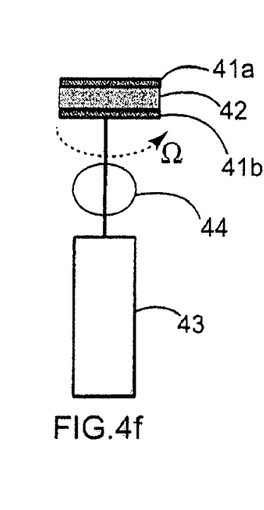
Figure 4G:
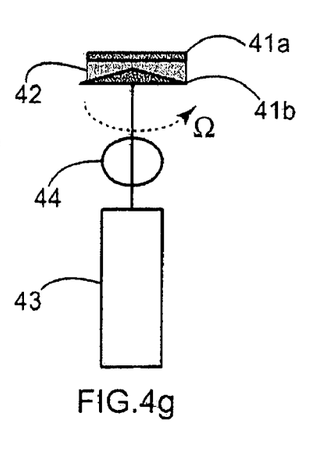

FIGS. 4*a* to 4*g* show various embodiments of devices according to the invention. In particular:

FIG. 4*a* corresponds to a device in which the sample 42 is placed between two horizontal interaction surfaces 41*a* and 41*b*, which move relative to each other (translational movement);

FIG. 4*b* corresponds to a device in which the sample 42 is placed between two vertical interaction surfaces 41*a* and 41*b* between which the sample flows or is displaced;

FIG. 4*c* corresponds to a device in which the sample 42 is placed between two coaxial cylinders 41*a* and 41*b* rotating one with respect to the other (Couette geometry);

FIG. 4*d* corresponds to a ball moving through a sample: in this case, there is only one interaction surface 41 between the device and the sample 42; and FIGS. 4*e* to 4*g* correspond to devices in which the sample 42 is placed between two horizontal interaction surfaces 41*a* and 41*b* rotating one with respect to the other. The device of FIG. 4*g* is characterized by a cone/plate interaction geometry, whereas the devices of FIGS. 4*e* and 4*f* have a plate/plate geometry.

The relative movement between the interaction surface and the sample may be a rotation or a translation. In the case of a rotation, the sample undergoes, on the periphery, a larger displacement Δ1 than at the center of rotation (Δ1 is proportional to the radius), irrespective of the geometry (plate/plate or cone/plate in the latter case, the strain rate is maintained).

The slip conditions vary depending on the distance from the center of rotation, the risks of slip between the sample and the interaction surface being greater at the edges. This difficulty is absent in the case of a translation, since the displacement is identical at all points on the surface, and therefore the slip conditions are themselves also uniform. Advantageously, the displacement will therefore be a translation. According to one preferred mode of implementation, the displacement is of the oscillatory type in order to obtain the viscoelastic properties (elastic modulus and loss modulus) under unperturbating conditions (also called the linear regime, generally obtained by applying an oscillation of very low amplitude). According to another mode of implementation, the movement is of the continuous type in order to obtain the flow properties of the material (viscosity, yield stress).

Advantageously, the device includes at least one sensor 44 for measuring at least one physical quantity, in particular a dynamic or kinematic quantity, of a sample 42 and/or of an interaction surface 41*a* and 41*b*. Preferably, the device includes at least a means for applying a displacement to at least one interaction surface or to the sample. Advantageously, this means 43 may be a mass under gravity (FIG. 4*d*) or a motor. It is particularly advantageous for said at least one motor and at least one sensor to be axially mechanically independent while still being able to be coaxial (FIG. 4*f*).

The force sensor 44 and the motor 43 are preferably placed along the same axis (FIGS. 4*e*, 4*f* and 4*g*), the sensor then measuring the mechanical resistance, by a direct measurement of physical parameters such as the velocity and acceleration, induced by the sample during transmission of the strain or stress (force) applied by the motor. Advantageously, as in the case of the devices shown in FIG. 4*e*, the force sensor 44 and the motor 43 may be decoupled. Thus, the motor that deforms the sample may be connected to an independent interaction surface and the force sensor connected to another interaction surface. In this situation, the sensor provides a direct measurement of the force transmitted by the sample under deformation, since the measurement and the deformation are decoupled. In contrast, in the devices of FIGS. 4*f* and 4*g*, the force sensor 44 and the motor 43 are coaxial, but are not independent.

The modes of implementation shown in FIGS. 4*a* to 4*cp* and 4*e* to 4*f*, which include a motor for applying a movement or a force such as a strain or a stress, to the sample and a force sensor for making the dynamic measurements, and in which the interaction surface consists of two independent parts, namely plates (of plate/plate or cone/plate type) or cylinders (Couette geometry), in contact with which the sample is stressed, correspond to rheometers. The mode of implementation shown in FIG. 4*d*, in which the interaction surface is in the form of a probe (weight or ball) or a microprobe (in the case of microrheology) corresponds to a viscometer. The viscometer of FIG. 4*d* has no motor and simply takes advantage of gravity for performing the displacement.

The following example demonstrates the improvement in rheological response obtained thanks to the invention when using a standard rheometer having coaxial supports (plate/plate, cone/plate or Couette geometry). In addition to the standard (aluminum and stainless steel) supports, various components (plates and cones) made of $Al_2O_3$ ceramic were produced in order to compare the viscoelastic measurements. The sample studied contained no bubbles, microbubbles or cavities (confirmed by microscopy). The sample was then deposited on the supports and left at rest for several hours. In the case of supports of the plate/plate type, the thickness typically stressed was around 0.5 mm.

The purpose of the measurements was to characterize the dynamic properties of a system at equilibrium, that is to say in its unperturbed state. The response of the material subjected to a low-amplitude strain, that is to say in a regime for which the response is independent of the strain amplitude (linear regime), was examined. In practice, the rheometer imposed a sinusoidal strain $\gamma(\omega)$ of amplitude $\gamma_0$, by varying the frequency $\omega$ ($\gamma=\gamma_0 \sin \omega t$). It was therefore of paramount importance to ensure that the strain was correctly transmitted to the sample, that is to say that the interactions between the sample and the support corresponded to non-slip conditions. The sensor measured the response of the material, corresponding to a stress measurement containing two components, one component in phase with the strain (elastic modulus, denoted G') and one out of phase (viscous modulus, denoted G"). It was therefore also of paramount importance for the sample to transmit the deformation stress to the sensor without slip.

The results obtained with a standard surface, known from the prior art, and a surface with high wettability according to the invention (the shear thickness chosen was 0.1 mm) are the following:

In the case of standard metal supports, the conventional viscoelastic curve of a polymer, as described in the literature, was obtained. This curve had a terminal behavior (that is to say at low frequency) of the flow type (see FIG. 6*a*), the viscous modulus G" (□ symbols) decreasing with the frequency, and the elastic modulus G' (○ symbols) decreasing more rapidly with frequency (approaching a decrease as the square of the frequency), and having a negligible value compared with the viscous modulus. This description is in perfect agreement with the literature [J. D. Ferry, "Viscoelastic Properties of Polymers", published by Wiley, New York (1980)] and is assumed to represent the general behavior of any uncrosslinked polymer in the melt state.

Figure 6A:
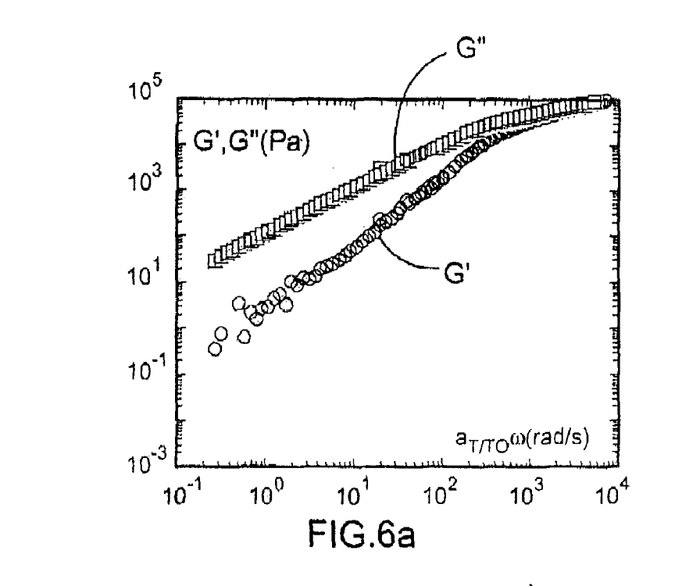
FIGS. 6a and 6b, viscoelastic curves showing the frequency dependence of the viscous and elastic moduli for (a) standard interaction surfaces made of aluminum and (b) interaction surfaces according to the invention, respectively.
Figure 6B:
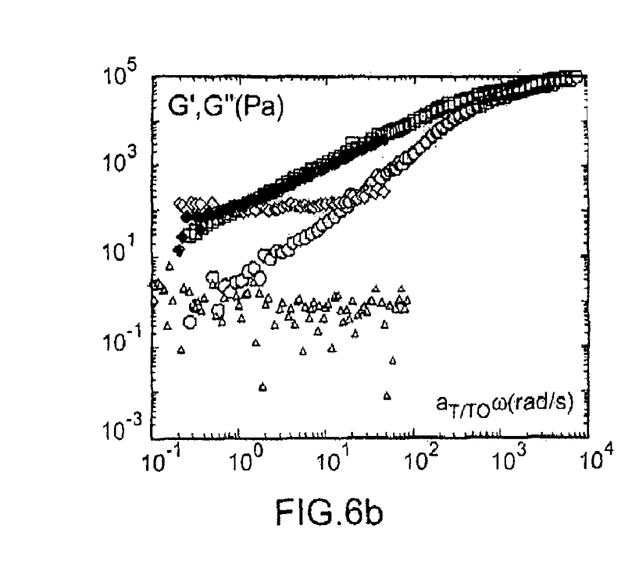

The rheological response of the same polymer (polybutyl acrylate) deposited on an $Al_2O_3$ ceramic support is illustrated by the symbols ◇ (in the case of G') and ◆ (in the case of G") in FIG. 6*b*. In the same figure, the symbol Δ represents the lower detection limit of the rheometer or a blank measurement, whereas ○ and □ represent the values of G' and G" measured using standard supports (same data as shown in FIG. 6*a*). The comparison of the two responses indicates a significant increase in the elastic modulus (G') when the polymer is deposited on the ceramic support. This increase in the modulus is due to better interaction between the polymer and its substrate. Instead of a typical flow behavior, corresponding to a decrease with the frequency of $G' \sim \omega^2$ as illustrated by the symbols ○ FIG. 6*a*, the curve corresponding to the variation of the elastic modulus as a function of frequency shows a behavior independent of frequency (elastic plateau), the elasticity of which corresponds to a modulus of ~100 Pa. There are more than 2 decades in difference between the lower measurement limit of the rheometer and the signal. This elastic plateau shows that the response of the polymer is independent of frequency, in other words this is a solid- or gel-type response. Put another way, the polymer is not a fluid as it does not flow, contrary to what is taught, rather it is a gel on macroscopic scales (tested up to thicknesses of about 0.5 mm) and this fundamental characteristic can be revealed only by optimizing the interaction conditions between the polymer and the sample support, as shown here.

Other polymers, such as polybutadiene and polystyrene, or various liquid crystal polymers, chemically different from polybutyl acrylate, and having different molecular weights, testify to a rheological response that confirms the identification of the elastic character of polymer melts [H. Mendil, P. Baroni and L. Noirez, to be published in Europhys. Lett., ibid to be published in Europhys. Phys. J. E].

Finally, these results, surprising as they are, since they are not compatible with the established models (Rouse dynamic model or de Gennes reptation model ["Scaling Concepts in Polymer Physics", Cornell University Press (1979)]), confirm and extend the first results obtained using a piezorheometer in a nonstandard manner [D. Collin & P. Martinoty, Physica A, 320, 235, (2003)]. This is because a conventional rheometer equipped with supports according to the invention is capable of identifying the elastic behavior reported [D. Collin & P. Martinoty, Physica A 320, 235, (2002)] not only on the scales studied by piezorheometry (which are limited to <100-150 µm) but also to much larger measurement scales, those commonly used in the laboratory or in industry (0.5 mm). For the same temperature difference from the glass transition temperature, i.e. $T-T_g=70°$ C., it should be noted that the elastic response observed by piezorheometry on treated surfaces (either grooved or electrostatically charged by friction or irradiation) can be measured only as far as 0.015 mm [D. Collin and P. Martinoty, Physica A 320, 235, (2003)]. The invention allows better optimization of the measurement compared with the recommended treatment for piezorheometer studies. Integrated into a conventional rheometer, the invention also guarantees better reliability of the measurements as a function of temperature, since the measurement performance is not impaired by the thermal variation, unlike a piezoelectric sensor, which also generally possesses pyroelectric properties (meaning that the piezoelectric constants are valid only within a restricted temperature range, becoming zero as the Curie temperature, generally around 200° C., is approached).

The examples described here confirm the benefit of the invention and reveal the scope of the discoveries that it can generate, more particularly here the generic character of the elastic nature of polymers, never identified hitherto by conventional rheology, and identified here at temperatures and on observation scales never achieved hitherto in the prior art.

The invention claimed is:

1. A method of determining at least one dynamic characteristic of a sample of a viscoelastic or fluid material, comprising the steps of:
    contacting said sample with at least one interaction surface;
    applying a relative movement between said sample and said interaction surface; and
    measuring at least one dynamic or kinematic quantity in respect of the sample and/or said interaction surface, and determining, from said measurement, at least one dynamic characteristic of said sample,
    wherein said interaction surface has an intrinsic wettability with respect to the sample that is higher than that of metal surfaces having a same roughness parameter.

2. The method as claimed in claim 1, wherein said interaction surface has a zero open porosity.

3. The method as claimed in claim 1, wherein said interaction surface has a surface energy at room temperature of greater than 1.2 J/m².

4. The method as claimed in claim 1, comprising the step of contacting said sample with at least two interaction surfaces and applying a relative movement between said two interaction surfaces.

5. The method as claimed in claim 1, wherein said dynamic or kinematic quantity is a relative quantity of the sample with respect to the interaction surface.

6. The method as claimed in claim 1, wherein said dynamic or kinematic quantity is chosen from a frequency, a stress, an amplitude, a strain, a velocity, an acceleration and a force.

7. The method as claimed in claim 1, wherein said interaction surface has an arithmetic mean roughness parameter of less than 12.5 µm.

8. The method as claimed in claim 7, wherein said interaction surface has an arithmetic mean roughness parameter of between 0.1 and 3.2 µm.

9. The method as claimed in claim 1, wherein said interaction surface consists of a single crystal.

10. The method as claimed in claim 9, wherein said single crystal is a single crystal based on silicon, germanium, oxides or carbides.

11. The method as claimed in claim 1, wherein said interaction surface consists of a high-density sintered ceramic.

12. The method as claimed in claim 11, in which said interaction surface consists of a high-density sintered ceramic essentially composed of oxides, nitrides and/or carbides and having a density of greater than 2.7.

13. The method as claimed in claim 11, wherein said ceramic consists of or is prepared from $Al_2O_3$, MgO, $SiO_2$, SiC, $ZrO_2$ or a mixture of these compounds.

14. The method as claimed in claim 11, wherein said ceramic is obtained by sintering at a pressure of 1 MPa or higher and at a temperature of 1500° C. or higher.

15. A device for determining at least one dynamic characteristic of a sample of a viscoelastic or fluid material, comprising
    at least one interaction surface intended to be brought into contact with said sample; and
    a means for imposing a relative movement between said sample and said interaction surface,
    wherein said interaction surface has an intrinsic wettability with respect to the sample that is higher than that of metal surfaces having a same roughness parameter.

16. The device as claimed in claim 15, wherein said interaction surface has a zero open porosity.

17. The device as claimed in claim 15, wherein said interaction surface has a surface energy at room temperature of greater than 1.2 J/m².

18. The device as claimed in claim 15, wherein said means for imposing a relative movement between said sample and said interaction surface includes a second interaction surface and a means for imposing a relative movement between said two interaction surfaces.

19. The device as claimed in claim 15, wherein said sensor is chosen from a force sensor, a torque sensor and a displacement sensor.

20. The device as claimed in claim 15, wherein said interaction surface consists of a single crystal.

21. The device as claimed in claim 20, wherein said single crystal is a single crystal based on silicon, germanium, oxides or carbides.

22. The device as claimed in claim 15, wherein said interaction surface has an arithmetic mean roughness parameter of less than 12.5 μm.

23. The device as claimed in claim 22, wherein said interaction surface has an arithmetic mean roughness parameter of between 0.1 and 3.2 μm.

24. The device as claimed in claim 15, further comprising at least one sensor for measuring at least one dynamic or kinematic quantity in respect of the sample and/or said interaction surface.

25. The device as claimed in claim 24, wherein said sensor and said means for imposing a relative movement between said sample and said interaction surface are placed on the same axis.

26. The device as claimed in claim 15, wherein said interaction surface consists of a high-density sintered ceramic.

27. The device as claimed in claim 26, wherein said interaction surface consists of a high-density sintered ceramic essentially composed of oxides, nitrides and/or carbides and having a density of greater than 2.7.

28. The device as claimed in claim 26, wherein said ceramic consists of or is prepared from $Al_2O_3$, $MgO$, $SiO_2$, $SiC$, $ZrO_2$ or a mixture of these compounds.

29. The device as claimed in claim 26, wherein said ceramic is obtained by sintering at a pressure of 1 MPa or higher and at a temperature of 1500° C. or higher.

* * * * *